United States Patent
Prough et al.

(10) Patent No.: US 10,206,607 B2
(45) Date of Patent: Feb. 19, 2019

(54) METHODS AND APPARATUS FOR OPTOACOUSTIC GUIDANCE AND CONFIRMATION OF PLACEMENT OF INDWELLING MEDICAL APPARATUS

(75) Inventors: Donald S. Prough, Galveston, TX (US); Rinat O. Esenaliev, League City, TX (US); Yuriy Petrov, Galveston, TX (US); Irene Petrov, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 180 days.

(21) Appl. No.: 14/114,454

(22) PCT Filed: Apr. 30, 2012

(86) PCT No.: PCT/US2012/035756
§ 371 (c)(1),
(2), (4) Date: Oct. 28, 2013

(87) PCT Pub. No.: WO2012/149519
PCT Pub. Date: Nov. 1, 2012

(65) Prior Publication Data
US 2014/0058253 A1 Feb. 27, 2014

Related U.S. Application Data

(60) Provisional application No. 61/480,482, filed on Apr. 29, 2011.

(51) Int. Cl.
*A61B 5/06* (2006.01)
*A61M 16/04* (2006.01)
(Continued)

(52) U.S. Cl.
CPC ............ *A61B 5/061* (2013.01); *A61B 1/0676* (2013.01); *A61B 1/07* (2013.01); *A61B 5/0095* (2013.01);
(Continued)

(58) Field of Classification Search
CPC ... A61B 5/0095; A61B 5/061; A61M 16/0488
(Continued)

(56) References Cited

U.S. PATENT DOCUMENTS 4,967,759 A 11/1990 Teves
5,193,544 A 3/1993 Jaffe
(Continued)

FOREIGN PATENT DOCUMENTS

EP 2701624 3/2014
WO 2006123282 A1 11/2006
(Continued)

OTHER PUBLICATIONS

Cardoso MM, et al "Portable Devices Used to Detect Endotracheal Intubation During Emergency Situations: a Review" Crit. Care Med. (1998) 26: 957-64.
(Continued)

*Primary Examiner* — Angela M Hoffa
(74) *Attorney, Agent, or Firm* — Thomas | Horstemeyer, LLP

(57) ABSTRACT

Medical apparatus are disclosed for optoacoustic monitoring of an indwelling unit of the apparatus, where the indwelling unit includes one or more optical components capable of directing pulsed light into an overlying tissue. The apparatus also include one or more acoustic components in contact with an exterior surface of the tissue to detect induced pressure waves producing an acoustic output analyzed with
(Continued)

an optoacoustic unit to monitor and confirm proper placement of the indwelling unit. Methods for using the apparatus are also disclosed.

18 Claims, 9 Drawing Sheets

(51) Int. Cl.
- A61B 5/00 (2006.01)
- A61B 1/06 (2006.01)
- A61B 1/07 (2006.01)

(52) U.S. Cl.
CPC .......... *A61B 5/06* (2013.01); *A61M 16/0411* (2014.02); *A61M 16/0488* (2013.01); *A61B 2505/05* (2013.01); *A61M 16/0434* (2013.01); *A61M 2205/3375* (2013.01); *A61M 2205/502* (2013.01); *A61M 2205/581* (2013.01); *A61M 2205/583* (2013.01)

(58) Field of Classification Search
USPC .................................................. 600/438, 473
See application file for complete search history.

(56) References Cited

U.S. PATENT DOCUMENTS

| | | | |
|---|---|---|---|
| 5,445,144 A | 8/1995 | Wodicka et al. | |
| 5,560,351 A * | 10/1996 | Gravenstein et al. ... | 128/200.26 |
| 5,785,051 A * | 7/1998 | Lipscher ............ | A61B 5/06 |
| | | | 128/200.26 |
| 5,840,023 A * | 11/1998 | Oraevsky et al. ............ | 600/407 |
| 6,161,537 A * | 12/2000 | Gravenstein et al. ... | 128/200.26 |
| 6,705,319 B1 * | 3/2004 | Wodicka et al. ........ | 128/207.14 |
| 7,037,271 B2 | 5/2006 | Crowley | |
| 7,068,867 B2 | 6/2006 | Avner | |
| 7,575,550 B1 | 8/2009 | Govari | |
| 7,729,738 B2 | 6/2010 | Flaherty et al. | |
| 7,930,035 B2 | 4/2011 | Dilorenzo | |
| 7,992,573 B2 * | 8/2011 | Wilson et al. ............... | 128/899 |
| 8,255,025 B2 * | 8/2012 | Villegas ........................ | 600/310 |
| 8,371,303 B2 * | 2/2013 | Schaner et al. .......... | 128/207.15 |
| 9,861,776 B2 * | 1/2018 | Lin ................... | A61M 16/0434 |
| 2003/0225320 A1 * | 12/2003 | Jeon ..................... | A61B 5/0059 |
| | | | 600/310 |
| 2004/0067000 A1 | 4/2004 | Bates | |
| 2004/0131299 A1 | 7/2004 | Adoram | |
| 2008/0072905 A1 | 3/2008 | Baker et al. | |
| 2008/0216826 A1 | 9/2008 | Boyden et al. | |
| 2009/0157059 A1 | 6/2009 | Allen et al. | |
| 2009/0227997 A1 | 9/2009 | Wang et al. | |
| 2010/0311026 A1 | 12/2010 | Tomes et al. | |
| 2011/0017217 A1 * | 1/2011 | Wood et al. ............. | 128/207.14 |
| 2012/0073572 A1 * | 3/2012 | Li ..................... | A61M 16/0418 |
| | | | 128/200.26 |
| 2012/0116156 A1 * | 5/2012 | Lederman ................ | A61B 1/05 |
| | | | 600/109 |
| 2012/0203101 A1 * | 8/2012 | Prough et al. ................. | 600/424 |
| 2012/0220845 A1 * | 8/2012 | Campbell ............ | A61B 5/0836 |
| | | | 600/364 |
| 2012/0302833 A1 * | 11/2012 | Hayman et al. .............. | 600/120 |
| 2014/0058253 A1 | 2/2014 | Prough | |

FOREIGN PATENT DOCUMENTS

| | | |
|---|---|---|
| WO | WO2009021064 A1 | 2/2009 |
| WO | 2012006607 A2 | 1/2012 |

OTHER PUBLICATIONS

Ezri T, et al "Use of the Rapiscope vs Chest Auscultation for Detection of Accidental Bronchial Intubation in Non obese Patients Undergoing Laparoscopic Cholecystectomy" J. Clin. Anesth. (2006) 18: 118-23.

Li J "A Prospective Multicenter Trial Testing the SCOTI Device for Confirmation of Endotracheal Tube Placement" J. Emerg. Med. (2001) 20(3): 231-9.

Milling TJ, et al. "Transtracheal 2d Ultrasound for Identification of Esophageal Intubation" J. Emerg. Med. (2007) 32: 409-14.

O'Connor CJ, et al "Identification of Endotracheal Tube Malpositions Using Computerized Analysis of Breath Sounds via Electronic Stethoscopes" Anesthesia and Analgesia (2005) 101(3): 735-9.

Reicher J, Et al "Use of Radio Frequency Identification (Rfid) Tags in Bedside Monitoring of Endotracheal Tube Position" J. Clin. Monit. Comput. (2007) 21:155-8.

Salem MR "Verification of Endotracheal Tube Position" Anesthesiol. Clin. North America. (2001) 19(4): 813-39.

Werner SL, et al "Pilot Study to Evaluate the Accuracy of Ultrasonography in Confirming Endotracheal Tube Placement" Ann. Emerg. Med. (2007) 49: 75-80.

PCT Search report and Written Opinion in corresponding PCT/US2011//043476, published as WO2012/006607.

PCT Search report and Written Opinion in corresponding PCT/US2012/035756, dated Aug. 31, 2012.

Foreign search results for PCT/US2012035756 dated Nov. 21, 2014.

Foreign search report CA 2,838,005 dated Mar. 13, 2017.

* cited by examiner

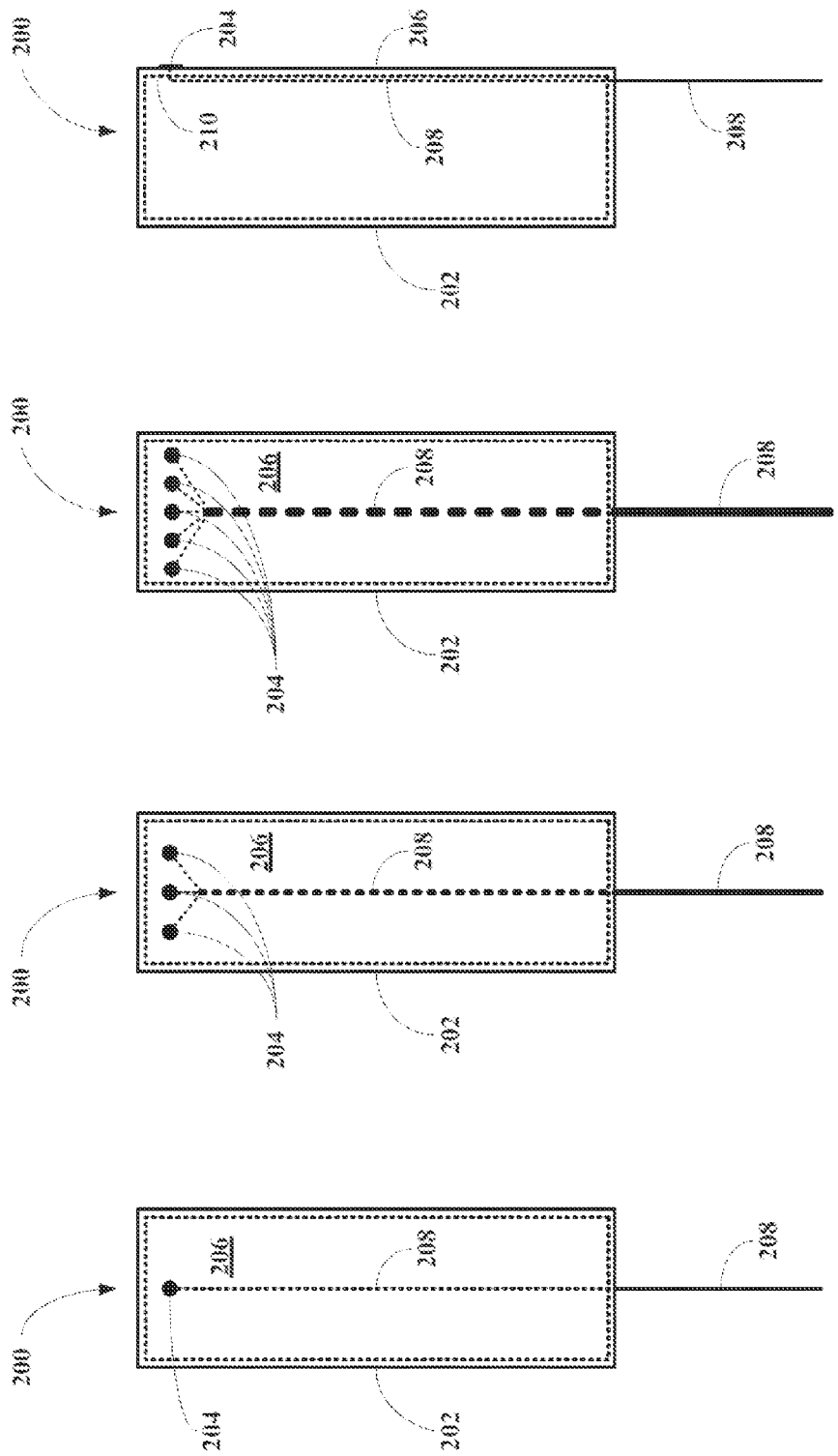

METHODS AND APPARATUS FOR OPTOACOUSTIC GUIDANCE AND CONFIRMATION OF PLACEMENT OF INDWELLING MEDICAL APPARATUS

CROSS REFERENCE TO RELATED APPLICATIONS

This application claims priority based on PCT/US12/035756, filed on Apr. 30, 2012, which in turn claims priority to U.S. Provisional Application Ser. No. 61/480,482 filed on Apr. 29, 2011, which applications are incorporated herein by reference.

FIELD OF THE INVENTION

This invention relates generally to apparatus and methods for guiding and confirming placement of medical devices. More particularly, embodiments of this invention relate to medical apparatus and methods that utilize optoacoustic guidance and confirmation of placement of endotracheal tubes and other indwelling medical devices.

BACKGROUND OF THE INVENTION

Without limiting the scope of the invention, its background is described in connection with existing methods and apparatus for guiding and confirming proper placement of medical apparatus that are inserted through a body channel or cavity.

Medical diagnosis and treatment frequently involve insertion of medical devices that are passed through naturally occurring channels and cavities in the patient's body. These include placement of catheters into large blood vessels such as through jugular, subclavian, antecubital and femoral sites. Cardiac catheterization involves passage of long catheters from peripheral insertion sites into the heart using X-ray visualization. Catheterization is also used to access the bladder and kidneys by retrograde passage through the urethra. Placement of nephrostomy tubes is typically done percutaneously into the renal pelvis under fluoroscopic or CT guidance. In any interventional procedure, insertion of the medical device into the proper location is critical. For example, improper placement or positioning of an endotracheal tube may be lethal.

Correct placement and positioning of an endotracheal tube is an essential component of life support during resuscitation from cardiac arrest, during stabilization and surgery after severe multiple trauma, during critical illnesses requiring airway and ventilatory support, during most surgical procedures under general anesthesia and during postoperative mechanical ventilatory support. To function properly in ventilating the lungs, an endotracheal tube must be inserted into the trachea, must be properly positioned in the midtrachea and must remain properly positioned until the endotracheal tube is no longer necessary. However, endotracheal tubes are often misplaced, particularly when placed in emergency circumstances, and endotracheal tube misplacement contributes to morbidity and mortality. Katz and Falk (Katz S H, Falk J L: "Misplaced endotracheal tubes by paramedics in an urban emergency medical services system" *Ann. Emerg Med.* (2001) 37:32-7) reported on a series over an eight-month interval of 108 patients who were intubated by emergency medicine personnel before arrival at a single-hospital Emergency Department (ED). On arrival at the ED, 25% (27/108) of endotracheal tubes were misplaced. Eighteen of 27 were in the esophagus; of those 18 patients, 56% died in the ED. In nine of the 27 endotracheal tubes were too deep (below the carina) or remained in the hypopharynx above the vocal cords; of those patients, 33% died in the ED. Li (Li J: "Capnography alone is imperfect for endotracheal tube placement confirmation during emergency intubation" *J. Emerg. Med.* (2001) 20:223-9) reported data, provided by the National Emergency Airway Registry database, regarding emergency endotracheal intubation performed in 24 participating hospital EDs from August 1997 to September 1999. Of 4,602 attempted emergency endotracheal intubations, the number of inadvertent esophageal intubations was 180, representing 4% of emergency intubations. Of these, ten (6% of all esophageal intubations) were initially unrecognized.

Misplacement of an endotracheal tube contributes to morbidity and mortality in several ways. Placement in the esophagus rather than in the trachea results in failure to effectively provide oxygen and remove carbon dioxide. Even a single breath administered while a tube is improperly positioned in the esophagus risks gastric inflation and promotes regurgitation and aspiration of gastric contents. Positioning of an endotracheal tube insufficiently far into the trachea risks laryngeal damage from cuff pressure on the structures in the larynx and, of greater immediate concern, risks accidental withdrawal into the pharynx. Positioning of an endotracheal tube too deeply may result in intubation of a main-stem bronchus, usually the right, causing hypoxemia because of failure to ventilate the opposite, usually the left, lung. Even a properly positioned endotracheal tube may subsequently move during taping (used to secure the endotracheal tube), retaping or changes in patient position. Misplacement after initial presumed placement most commonly occurs in obese patients, females, children and patients undergoing laparoscopy or placement in the Trendelenburg (head-down) position. See e.g. Weiss M, et al. "Clinical evaluation of cuff and tube tip position in a newly designed paediatric preformed oral cuffed tracheal tube" *Br. J. Anaesth.* (2006) 97:695-700. Because misplacement of an endotracheal tube can be lethal, proper positioning must be confirmed immediately after initial placement and must subsequently be monitored so that later tube displacement can promptly be recognized and corrected.

Proper insertion and positioning of endotracheal tubes is customarily performed or supervised by the most expert individual available, but expertise in endotracheal tube placement and maintenance varies widely by training and location. For respiratory support during surgery, placement is usually performed by anesthesiologists or nurse anesthetists, who typically are highly experienced and intubate patients on a daily basis. Moreover, during elective surgery, the risk is further reduced because most elective surgical patients have relatively good physiological reserves, surgical precautions reduce the risk of aspiration, and intubation is performed in highly controlled, nonemergency circumstances.

In hospitalized patients outside the surgery suite, endotracheal tube placement is usually performed as an emergency life-support procedure by a variety of physicians and nonphysicians, depending on the size and complexity of a hospital. Patients requiring emergency intubation usually have severe physiologic compromise, such as respiratory failure and cardiac arrest, and often must be intubated under poorly controlled circumstances by personnel with highly variable experience and expertise. These patients are particularly vulnerable to episodic hypoxemia. In EDs, placement is usually performed by emergency physicians, some of whom have considerable training, experience and expertise. However, some do not. In smaller hospitals during night shifts and on weekends, endotracheal tube placement is often performed by respiratory therapists, whose training varies widely and who may rarely have the opportunity to practice intubation.

In out-of-hospital situations, placement is usually performed by emergency medicine technicians or paramedics, whose experience and training often are limited. The inevitable disparities in experience and expertise between ED physicians, respiratory therapists, anesthesiologists and out-of-hospital emergency responders are compounded in emergency circumstances by less than optimal conditions and limited monitoring equipment. These important factors further reduce the chances of proper initial placement and subsequent maintenance of proper positioning of endotracheal tubes.

After endotracheal tube placement before surgery, patients subsequently remain in a highly monitored, stable environment, in which endotracheal tube position can be constantly monitored by an anesthesiologist or nurse anesthetist who can recognize tube displacement and intervene. Patients who are endotracheally intubated outside surgical suites or outside hospitals typically must be transported to other locations for definitive therapy, diagnostic imaging or intensive care. In each environment and during transport, because misplacement of an endotracheal tube can be lethal, proper positioning must be confirmed immediately after initial placement and must subsequently be monitored so that later tube displacement can promptly be recognized and corrected. Currently available technology is unsuitable for monitoring of endotracheal position, especially by personnel of limited experience.

The current gold standards of clinical practice for confirmation of endotracheal tube position include: (1) direct visualization of the endotracheal tube entering the trachea, (2) auscultation to confirm bilateral, symmetrical breath sounds and absence of air entry over the epigastrium (to exclude esophageal intubation), (3) detection of exhaled carbon dioxide to confirm placement in the lungs, (4) fiberoptic confirmation by visualization of the trachea and mainstem bronchi, and (5) chest radiography. Of these techniques, only fiberoptic airway examination and chest radiography provide direct information of proper positioning in the mid-trachea.

Salem (Salem M R. "Verification of endotracheal tube position" *Anesthesiol. Clin. North America* (2001) 19:813-39) has summarized the pitfalls of each of these techniques. Although each is relatively reliable, each also is associated with errors, the consequences of which can be grave. In some patients, visualization of the larynx is inadequate to confirm endotracheal tube placement. Direct visualization of an endotracheal tube passing the cords requires expertise in laryngoscopy, is sometimes difficult or impossible to achieve, and cannot be performed repeatedly. Fiberoptic bronchoscopy requires technical expertise, interferes with ventilation, and cannot be performed continuously. Chest radiography is intermittent, requires movement of a patient to perform radiography, and does not provide rapid feedback.

Auscultation is prone to both false-positive and false-negative findings. The dramatic decrease in respiratory complications of anesthesia during the past thirty years is certainly attributable in part to expeditious recognition and correction of esophageal intubation, although anesthesia personnel continue to be challenged by difficulty in confirming endotracheal tube placement in the mid-trachea, especially in circumstances in which post-intubation movement of a patient can result in movement of the tube within the trachea.

The challenges of recognizing esophageal intubation and endotracheal tube movement are much greater in emergency circumstances outside the operating room. Detection of exhaled carbon dioxide by capnography functions well in physiologically stable patients during surgical anesthesia. However, in emergency circumstances, especially during cardiac arrest, capnography is less reliable because carbon dioxide exhalation is highly variable and requires ventilation. In patients during cardiac arrest, minimal carbon dioxide may be exhaled through the lungs and use of this method provides a substantial incidence of false-positive and false-negative results in emergency intubations. Li quantified the sensitivity and specificity of capnography when used in emergency circumstances. (Li J: supra) Based on a meta-analysis of capnography trials that included 2,192 intubations, the sensitivity for confirmation of endotracheal intubation was 93% (95% confidence interval 92-94%), and the specificity was 97% (CI 93-99%). Therefore, for emergency intubations, the false-negative failure rate (tube in trachea but capnography indicates esophagus) was 7%, and the false-positive rate (tube in esophagus but capnography indicates trachea) was 3%.

To address the clinical problems of promptly recognizing initial endotracheal tube misplacement or subsequent endotracheal tube displacement, a variety of technological aids have been suggested or developed to supplement or replace auscultation and quantitative capnography. See e.g. O'Connor C J, et al. "Identification of endotracheal tube malpositions using computerized analysis of breath sounds via electronic stethoscopes" *Anesthesia and Analgesia* (2005) 101:735-9; Cardoso M M, et al. "Portable devices used to detect endotracheal intubation during emergency situations: a review" *Crit Care Med.* (1998) 26:957-64; Ezri T, et al. "Use of the Rapiscope vs chest auscultation for detection of accidental bronchial intubation in non-obese patients undergoing laparoscopic cholecystectomy" *J Clin. Anesth.* (2006) 18:118-23; Reicher J, et al. "Use of radio frequency identification (RFID) tags in bedside monitoring of endotracheal tube position" *J Clin. Monit. Comput.* (2007) 21:155-8; Werner S L, et al. "Pilot study to evaluate the accuracy of ultrasonography in confirming endotracheal tube placement" *Ann. Emerg Med.* (2007) 49:75-80; Li J. "A prospective multicenter trial testing the SCOTI device for confirmation of endotracheal tube placement" *J Emerg Med.* (2001) 20:231-9; and Milling T J, et al. "Transtracheal 2-D ultrasound for identification of esophageal intubation" *J. Emerg. Med.* (2007) 32:409-14).

The principles of operation of the devices vary. Some qualitatively detect exhaled carbon dioxide, some utilize transmission of light from within the trachea to the skin surface, some depend on aspiration of air from the trachea, and some are based on ultrasonography. The Sonomatic Confirmation of Tracheal Intubation (SCOTI) device connects to the end of the endotracheal tube and assesses the air content of the structure within which the endotracheal tube is located, i.e., within the rigid, air-filled trachea or the flaccid esophagus. However, the SCOTI device requires disconnection from the ventilator, only differentiates esophageal from tracheal intubation, has an appreciable false-positive and false-negative rate and does not indicate proper position within the trachea. Ultrasound-based techniques require expertise in ultrasonography and are not suitable for continuous monitoring.

Although all approaches offer advantages and provide feedback that can be helpful, no single device is sufficiently reliable to be considered the standard of care and some, such as fiberoptic bronchoscopy, require substantial skill and training.

Thus, there is a real need in the art for an easy method for monitoring and confirming proper placement of indwelling medical apparatus in a mammalian body including a human body.

SUMMARY OF THE INVENTION

In certain embodiments provided herein, medical apparatus adapted for insertion through a body channel or cavity are provided with tracking capability based on optoacoustic monitoring. In one embodiment, indwelling units having at least one optical component are provided. In certain embodiments, the apparatus also includes a light source in communication with the optical component via a light conduit for generating electromagnetic radiation. An acoustic component is placed on a site of a patient's body overlying an internal placement site for the indwelling unit. A receiver/analyzer unit is utilized for receiving an output signal from the acoustic component and converting the signal into information concerning an internal location of the indwelling unit. The optical component directs electromagnetic radiation (light) into soft tissue overlying the placement site of the indwelling unit. In response to the absorbed pulsed electromagnetic radiation in the overlying soft tissue, spatially resolved pressure signals are produced in the tissue. The spatially resolved pressure signals are received as acoustic signals by the acoustic component and analyzed by the receiver/analyzer unit. In certain embodiments, the optical component generates electromagnetic radiation in the form of pulsed laser light that generates an acoustic component in the form of an ultrasound pressure signal.

In certain embodiments disclosed herein, a system for real-time placement tracking of indwelling medical devices is provided that includes an indwelling medical device, one or more optical components affixed to the indwelling medical device and adapted to emit electromagnetic radiation and thereby generate an acoustic signal in a tissue receiving the indwelling medical device, one or more external acoustic detectors adapted to receive the acoustic signal generated in the tissue; and an analyzer in electrical communication with the one or more detectors, wherein the analyzer is adapted to produce an output that reflects placement of the medical device. The analyzer may include or be connected to a display screen. In some embodiments a visual tracking output is provided while in other embodiments the analyzer generates a range of audible signals including a safety tone that indicates desired placement of the indwelling device and an alarm tone that indicates improper placement of the indwelling device. The visual display may be combined with audible signals if desired.

In some embodiments, the system further includes a light conduit in optical communication with the optical component and adapted for connection to, and transmittal of light from, a light source external to the patient's body. One example of a suitable light conduit is a fiber optic. In alternative embodiments the light source is not located remotely but instead generates light locally from inside the patient's body. In certain embodiments the electromagnetic radiation is pulsed laser light at a near- to mid-infrared wavelength from about 750 nm to about 2500 nm.

Embodiments of the present invention provide methods for placing and monitoring the placement of indwelling medical unit including at least one optical component utilized in conjunction with an acoustic component placed on a site of a patient's body overlying an internal placement site for the indwelling unit and analyzed by the receiver/analyzer unit. The methods also include inserting the indwelling unit into a body of an animal (e.g., a human or other mammal) and monitoring the insertion via the acoustic component. The methods also include confirming placement of the indwelling unit by optoacoustic monitoring. The methods may optionally include continuous, periodic, and/or intermittent monitoring of the indwelling unit to ensure maintained proper unit placement.

In certain embodiments, the indwelling medical unit is an endotracheal tube having a cuff including the optical component or a plurality of optical components, where the components are disposed to direct pulsed light into the soft tissue overlying the internal placement site in proximity of the acoustic component. The pulsed light induces spatially resolved pressure signals in the tissue. The acoustic signals are received by the acoustic component the output of which is forwarded to that receiver/analyzer unit. The receiver/analyzer unit generates information utilized to confirm that the cuff or the endotracheal tube is properly positioned in a mid-trachea and is not accidentally positioned in the esophagus. Continuous, periodic or intermittent optoacoustic monitoring may be used to ensure that the cuff or tube has not moved out of its proper position.

BRIEF DESCRIPTION OF THE DRAWINGS

The invention can be better understood with reference to the following detailed description together with the appended illustrative drawings:

FIGS. 2A-D depict embodiments of optical components for optoacoustic monitoring.

DETAILED DESCRIPTION OF THE INVENTION

Figure 1:
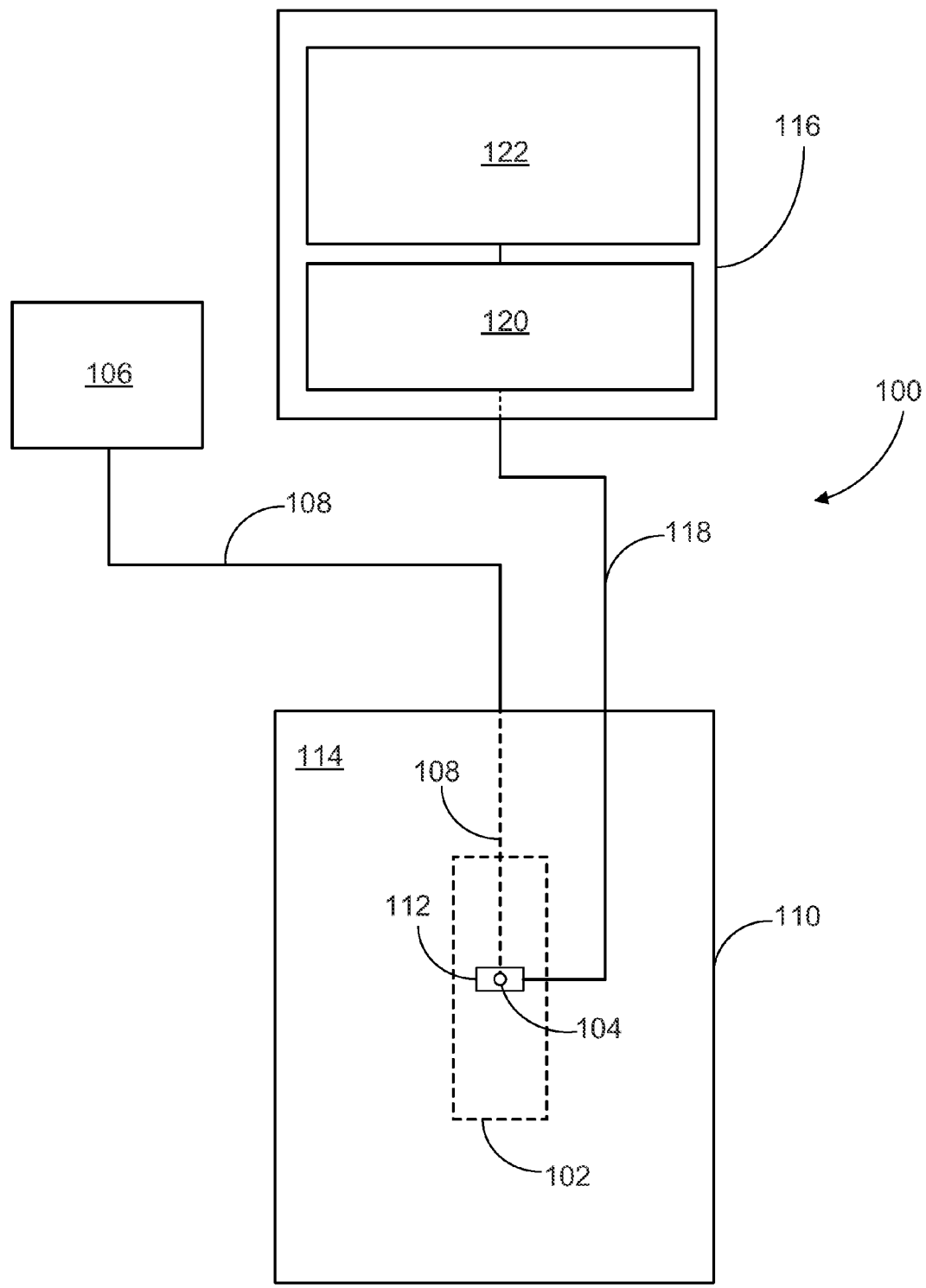
FIG. 1 depicts an embodiment of an apparatus that utilizes optoacoustic monitoring for placement and monitoring of medical devices placed in the body.

The inventors have found that an optoacoustic method can be implemented for confirming and monitoring of placement of indwelling medical apparatus. In certain embodiments of this optoacoustic methodology, confirming and monitoring is directed to a proper placement of endotracheal tubes in children and adults as an example of the general use of optoacoustic methods of this invention for confirming and monitoring placement of indwelling medical apparatus.

Embodiments of the present invention broadly relate to medical apparatus including an indwelling unit having at least one optical component (one optical component or a plurality of optical components). The apparatus also include a receiver/analyzer unit having at least one acoustic component (one acoustic component or a plurality of acoustic components). The apparatus also include a source of electromagnetic radiation (e.g., pulsed light) connected to the optical components via one or more light conduits. The optical components direct the electromagnetic radiation into a tissue overlying an internal indwelling unit placement. The electromagnetic radiation pulse induces spatially resolved pressure signals in the tissue. The acoustic signals are received by the acoustic component, the output of which is forwarded to that receiver/analyzer unit. The receiver/analyzer unit generates information utilized to confirm that the indwelling unit is properly positioned. For example, an endotracheal tube should be positioned in the mid-trachea, not the esophagus. Continuous, periodic or intermittent optoacoustic monitoring may be used to ensure that the cuff or tube has not moved out of its proper position.

Embodiments of the present invention broadly relate to methods for placing and monitoring the placement of indwelling medical apparatus. The methods include providing a medical apparatus including an indwelling unit having an optical component or a plurality of optical components. The apparatus also include a receiver/analyzer unit having an acoustic component or plurality of acoustic components. The apparatus also include a source of electromagnetic radiation (e.g., pulsed light) connected to the optical components via one or more light conduits. In certain embodiments, the electromagnetic radiation comprises near-infrared light (the optical component of the optoacoustic technique), and pressure signal comprises an ultrasound signal (the acoustic component of the optoacoustic technique). The methods also include inserting the indwelling unit into a body of an animal so that the optical component is capable of directing pulsed light into surrounding tissue. The methods also include monitoring the insertion via the receiver/analyzer, which receives acoustic signals from the acoustic components. The acoustic signals comprise spatially resolved pressure signals induced in the surrounding tissue by the pulsed light from the optical components. The methods also include confirming placement of the unit through optoacoustic monitoring. The methods may optionally include continuous, periodic, and/or intermittent monitoring of the indwelling unit to ensure the indwelling unit is maintained in a proper placement. In certain embodiments, the indwelling unit is an endotracheal tube having a cuff including an optical component or a plurality of optical components, where the components direct pulsed electromagnetic radiation (light) into the surrounding tissue. The methods can be used to ensure that the cuff or the endotracheal tube is properly positioned in a mid-trachea and is not accidentally positioned in the esophagus via the optoacoustic monitoring of the acoustic signals.

In certain embodiments, the medical apparatus includes an endotracheal tube including a cuff, where the cuff includes an optical component or a plurality of optical components. The apparatus also include a receiver/analyzer unit having an acoustic component or a plurality of acoustic components. The optical components direct pulsed electromagnetic radiation (light) into surrounding tissue. The pulsed light induces spatially resolved pressure signal in the tissue in response to the absorbed pulsed electromagnetic radiation. The acoustic components detect he pressure signals. The receiver/analyzer receives an output from the acoustic components and analyzes the output to determine and monitor tube placement. The monitoring is used to guide and confirm placement of endotracheal tube and to continuously, periodically and/or intermittently monitor tube placement. The frequency of the pressure signal induced in the tissue is controlled by the wavelength of the pulsed light. In certain embodiments, the pulsed light produces ultrasonic signals in the tissue. The acoustic components are then positioned on the anterior neck to provide rapid initial assessment and subsequent intermittent, periodic, or continuous feedback regarding the positioning of the cuff of the endotracheal tube. The inventors have demonstrated that the systems and methods of this invention are capable of confirming the proper placement of the cuffs or endotracheal tubes in the mid-trachea thereby reducing or eliminating accidental placement of the cuffs or endotracheal tubes in the esophagus.

There are several characteristics of optoacoustic technology and of the human trachea and esophagus that make optoacoustic technology ideally suited for confirming and monitoring proper placement of indwelling units placed in the trachea or for placement of any other indwelling apparatus in its intended location in the body of a human, a mammal, or animal. Optoacoustic technology is based on the fact that when pulsed electromagnetic radiation such as, for example, pulsed light, encounters a chromophore or pigment, the radiation is absorbed producing a pressure wave, which is detectable as an acoustic response. In certain embodiments, the pulsed electromagnetic radiation is in the range of infrared light, which is defined as having a wavelength from 750 nm (the upper most wavelength of the visible light range, which is considered to be in the range of about 390-750 nm) to 1 mm (beginning of microwave portion of the electromagnetic spectrum). In certain exemplified embodiments, the pulse electromagnetic radiation is provided by one or more sources of laser light emitting in the near to mid-infrared (from 750 nm to 2500 nm). Laser optoacoustic technology combines certain advantages of the high optical contrast of optical tomography with the minimal scattering of acoustic waves found in ultrasound imaging to yield high contrast, sensitivity, and resolution. Laser optoacoustics techniques utilize the sensitive detection of laser-induced ultrasonic waves, which travel without scattering through tissue in a straight line from the source to the transducer. Several wavelengths in the near to mid-infrared range (ranging from about 750 nm to about 2500 nm) have been tested successfully and it is expected that other wavelengths will be suitable. Nd:YAG (neodymium-doped yttrium aluminium garnet) lasers having a typical wavelength of 1064 nm have been utilized effectively as well as pulsed laser diodes emitting at a wavelength of around 1550 nm. Compact solid state laser diodes are presently available that emit in a large number of discrete wavelengths beginning in the visible light range of from about 375 nm though the lower end of the infrared range up to about 1550 nm.

Depending on the wavelength and duration, the acoustic response may have a different frequency band. In embodiments involving tissues in mammalian bodies, human bodies or animal bodies, the properties of the pulsed light (including wavelength and duration) are generally adjusted to induce an ultrasonic response (ultrasonic waves). The ultrasound waves travel in straight lines from their source with minimal scattering and attenuation, thereby providing both lateral resolution and axial resolution regarding the size and shape of the source. The ultrasound waves are then detected by the acoustic components in contact with or close proximity of the tissue surrounding the indwelling unit. The acoustic components in turn generate an output that is received by the receiver/analyzer unit, which converts the output into information concerning the position of the indwelling unit.

Ultrasound waves propagate through tissue, but are effectively blocked by air. The trachea is an air-filled cylinder that lies immediately beneath the anterior surface of the neck. When the cuff of an endotracheal tube is inflated, the cuff directly seals against the interior surface of the trachea, thereby bringing the optical components into direct contact with or in close proximity to the tissue surrounding the cuff. The pulsed light irradiates the tissue producing ultrasonic pressure waves. The ultrasonic waves have a short, direct propagation path in tissue. The ultrasonic waves are then detected at the surface of the neck by the acoustic component or detector. Within a few seconds or less, an optoacoustic assessment can confirm whether the cuff of the endotracheal tube is in a proper position within the trachea (see FIGS. 3A and 3B) and is not in the esophagus or that it is not inserted too deeply or too shallowly. For guidance of intubation, the light source is generally located external to the body and is connected to the optical components of the cuff via optical light conduits such as fiberoptic conduits. In certain embodiments, the tube may include a light source generator if the generator is small enough to avoid interference with physical structures in the patient or would otherwise complicate the underlying procedure. For confirming and monitoring of endotracheal tube position, the pulsed near-infrared light source can be incorporated into the receiver/analyzer unit or can be a standalone component.

Optoacoustic guidance of endotracheal intubation and confirming and monitoring of endotracheal tube position disclosed herein has the following attributes: (1) easy to use with minimal training, (2) negligible incidence of false-positive and false-negative results, (3) nearly instantaneous feedback regarding endotracheal tube position, (4) effective confirmation of initial endotracheal tube placement at a proper cephalad/caudad orientation, (5) continuous monitoring to detect subsequent cephalad or caudad displacement, (6) no requirement for ventilation to detect endotracheal tube placement, (7) no requirement for temporary disconnection from ventilation to confirm or monitor endotracheal tube placement and (8) no requirement for patient transportation or movement to determine endotracheal tube position.

Endotracheal tube placement is a specific example of placement of a medical apparatus or foreign body within tissues with the subsequent need to non-invasively confirm correct placement. Optoacoustic technology is ideally suited to any clinical situation in which a foreign body is placed within a human, mammal, or animal body for medical purposes, e.g., intravascular catheters, urinary bladder catheters, drainage tubes or prosthetic devices, and in which subsequent noninvasive confirmation of proper placement is required.

Certain of the present inventors were the first to propose the optoacoustic technique for confirmation and monitoring of correct placement of indwelling medical devices such as endotracheal tubes in children and adults. In a previous application, U.S. application Ser. No. 13/179,482 and PCT/US2011/043476, incorporated herein by reference, certain of the present inventors disclosed the use of optoacoustic technology to detect pigmentation added to indwelling medical devices for the purpose of generating an optoacoustic signal. The present application provides an alternative technique to confirm placement of indwelling medical devices, such as endotracheal tubes, by generating an optoacoustic signal in water in tissue irradiated by an optical source.

The medical apparatus of this invention include at least: (1) at least one optical component disposed in or on an indwelling unit or adapted to be attached to an indwelling unit, (2) a pulsed near-infrared light source in optical communication with the optical component, (3) at least one acoustic component capable of being disposed on a second site of a human, mammal or animal body overlying a first site of the body where the indwelling unit is to be placed, and (4) an optoacoustic receiver/analyzer. In the case of an endotracheal tube, in certain embodiments, the cuffs of endotracheal tubes are modified by adding an optical component or a plurality of optical components. The optical components can generate pulsed light directly or may be in optical communication with a separate light source. The separate light source is capable of generating pulsed electromagnetic radiation of a defined wavelength or wavelength range (discretely populated or continuous) at a defined duration and defined pulse repetition rate. The light source can either be associated with the endotracheal tube or generally external to the body. Optical communication may be effectuated by any light conduit capable of transmitting the pulsed light generated by the light source to the optical components. As stated previously, the optoacoustic methods of this invention are based on the fact that pulsed light such as pulsed near infrared light emitted by the optical component into a tissue (the optical feature of the optoacoustic technique) induces spatially resolved acoustic (pressure) signals in the tissue (the acoustic feature of optoacoustic technique).

Referring now to FIG. 1, an embodiment of an optoacoustic monitoring apparatus, generally 100, is shown to include an indwelling unit 102 having an optical component 104 connected to a pulsed light source 106 via a light conduit 108. The indwelling unit 102 is depicted disposed behind an overlying tissue 110, that is, the indwelling unit 102, has been inserted into a human, mammal or animal so that the optical component 104 is capable of directing pulse light into the overlying tissue 110. The apparatus 100 also includes an acoustic detector 112 shown here situated on an exterior surface 114 of the overlying tissue 110. The acoustic detector 112 is in electrical communication with an optoacoustic unit 116 via a cable 118. The optoacoustic unit 116 includes a receiver/analyzer unit 120 and a display 122. The receiver/analyzer unit 120 receives and analyzes an acoustic signal detected by the acoustic detector 112. The acoustic signals comprise spatially resolved pressure waves induced in the tissue 110 by the pulsed light directed into the tissue by the optical component 104. Of course, the light source 106 may be incorporated into the optoacoustic unit 116. In any event, the pulse rate and frequency of the light is controlled by the optoacoustic unit 116 and by the constraints of the light source 106. In certain embodiments, the light is near infrared and the duration is in the range from one nanosecond to hundreds of nanoseconds to induce ultrasonic waves in the tissue 110.

Moreover, there may be a plurality of optical components and/or a plurality of acoustic components. Furthermore, each optical component may direct different pulsed light into the overlying tissue, and each acoustic component may be tuned to receive acoustic signal induced by one of the optical components to achieve frequency discrimination.

Embodiments of General Indwelling Units

Referring now to FIGS. 2A-C, three embodiments of indwelling units with optoacoustic monitoring capability, generally 200, are shown in top plan view. In FIG. 2D, a side plan view of the three embodiments is also shown. Looking at FIG. 2A, unit 200 includes a housing 202 to be disposed in an interior tissue or organ site of a human, mammal or animal. Unit 200 also includes an optical component 204 disposed on an outer surface 206 of housing 202. The optical component is in light communication with a light source (not shown) via optical conduit 208. Looking at FIG. 2B, unit 200 includes housing 202 to be disposed in an interior tissue or organ site of a human, mammal or animal. Unit 200 also includes three optical components 204 disposed on outer surface 206 of housing 202. The optical component is in light communication with a light source (not shown) via optical conduit 208. Looking at FIG. 2C, unit 200 includes housing 202 to be disposed in an interior tissue or organ site of a human, mammal or animal. Unit 200 also includes five optical components 204 disposed on an outer surface 206 of housing 202. The optical component is in light communication with a light source (not shown) via optical conduit 208. Looking at FIG. 2A, units 200 of FIGS. 2A-C are shown in a side view, where light conduit 208 is situated long inner wall 210 of housing 202.

Endotracheal Embodiments

To guide and confirm placement of endotracheal tubes and continuous or intermittent monitoring of correct placement, pulsed laser light is directed from within an endotracheal tube at the soft tissue that overlies the trachea. The pulsed laser light subsequently generates a spatially resolved ultrasound signal upon encountering tissue water, which acts as a chromophore. The pulsed laser light source is incorporated into or onto an existing medical device, such as an endotracheal tube, or will be part of a purpose-built optoacoustic probe that will be inserted into or onto the endotracheal tube such that pulsed laser light source is located directly parallel to the endotracheal tube cuff or to an analogous position on an uncuffed tube. In addition, an acoustic detector will be positioned on the anterior neck to provide rapid initial assessment and subsequent intermittent or continuous feedback regarding the positioning of the cuff of the endotracheal tube, demonstrating that the cuff or the endotracheal tube is properly positioned in the mid-trachea and is not accidentally positioned in the esophagus.

Figure 3A:
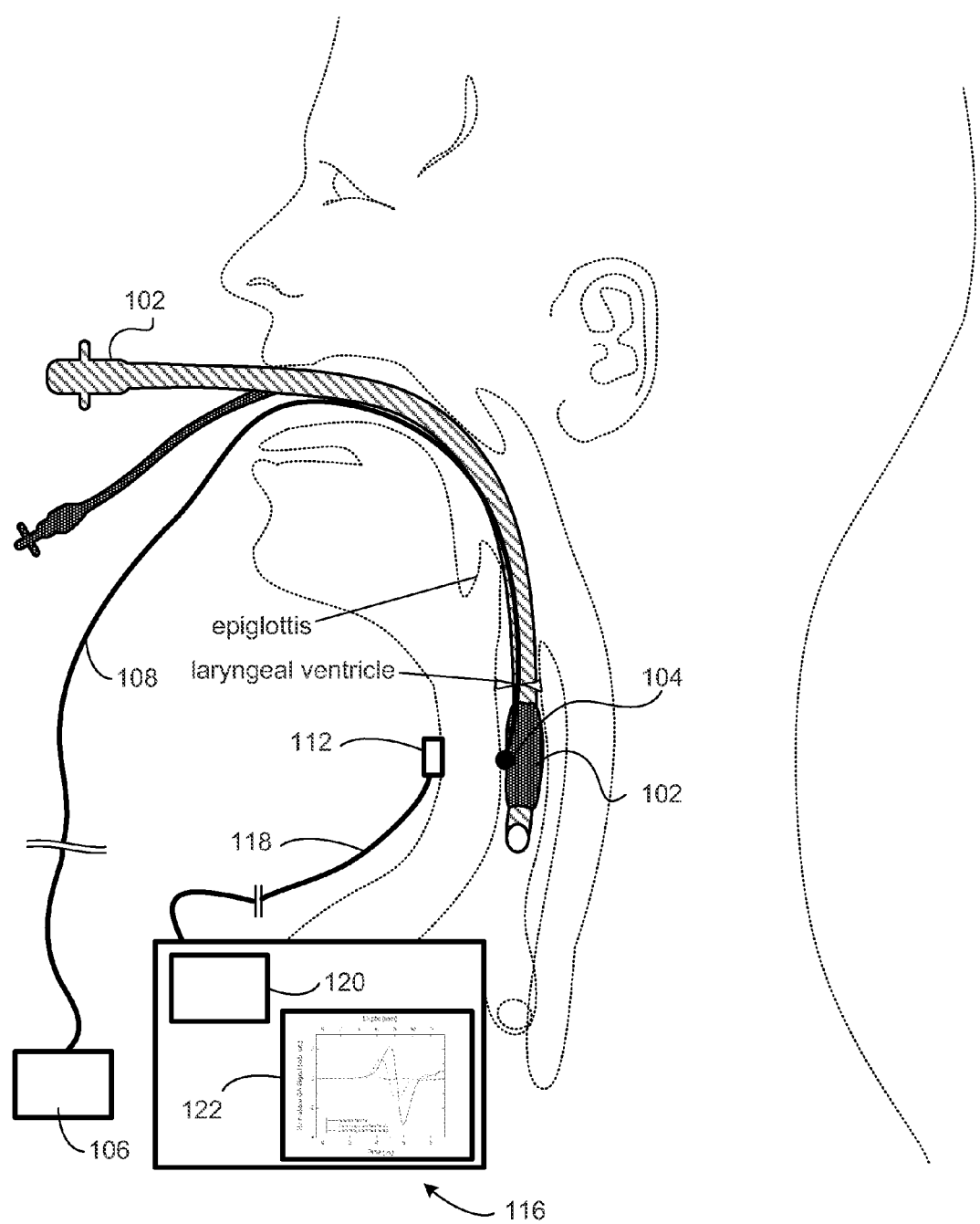
FIG. 3A shows the relative placement of the optical transmitting elements and the acoustic receiving elements in relation to a patient during placement of an endotracheal tube.

FIG. 3A shows the relative placement of the optical transmitting elements and the acoustic receiving elements shown in FIG. 1 in relation to a patient during placement of an endotracheal tube.

Figure 3B:
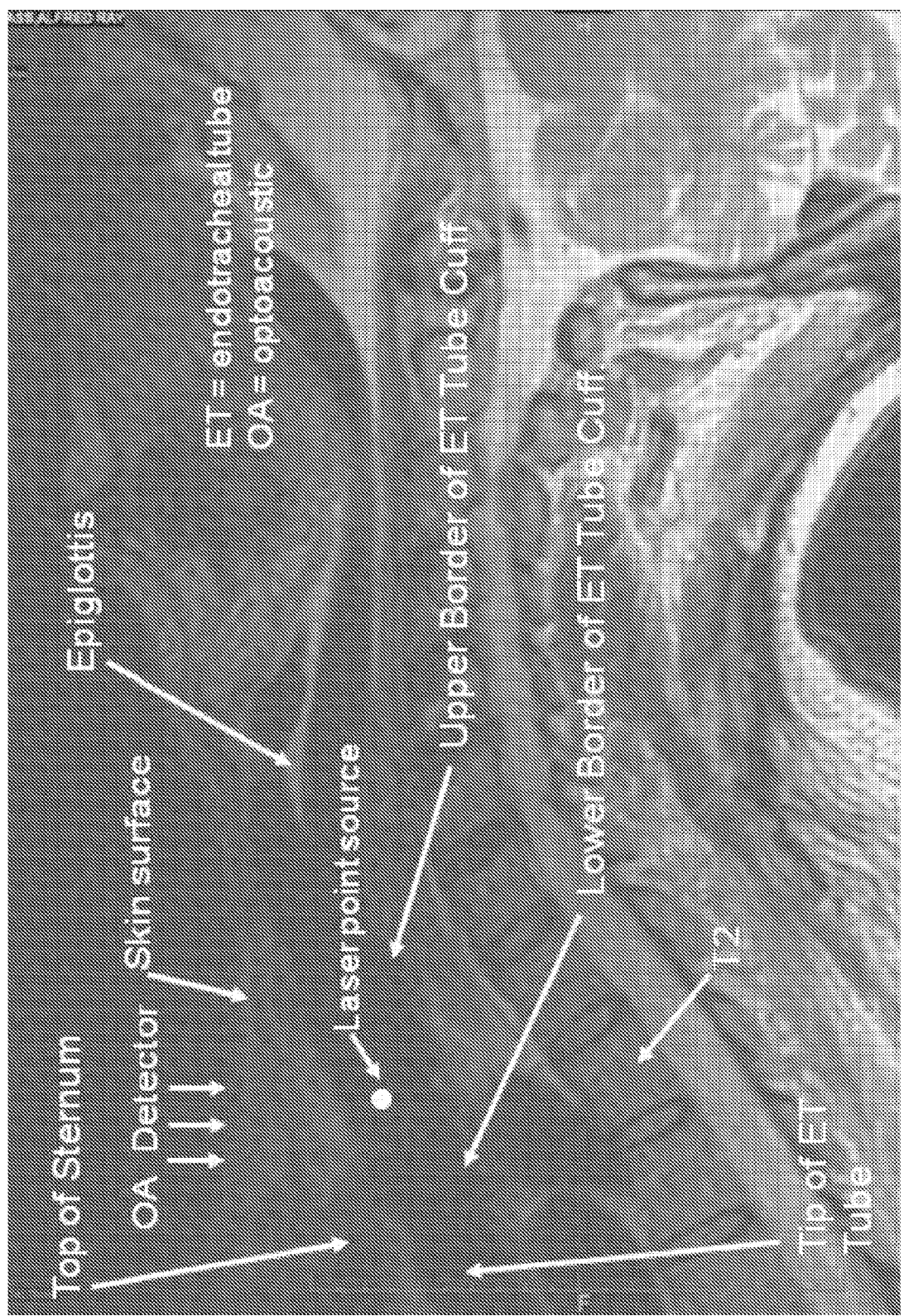
FIG. 3B shows by magnetic resonance imaging (MRI) an embodiment of an endotracheal apparatus placed in a trachea of a patient showing the acoustic components and optical components.

Referring now to FIG. 3B, a magnetic resonance image (MRI) of a patient with an endotracheal tube in place is shown. The tube itself is not visible because the plastic does not generate a signal. If an endotracheal tube is properly placed, an optical source that is positioned within the endotracheal tube at a location that is approximately in the middle of the endotracheal tube cuff will generate signals in water in an overlying tissue that are then detectable at an acoustic component as optoacoustic (OA) signals on the exterior skin of the neck or overlying tissue.

Such a device can also be used to facilitate endotracheal intubation, confirmation and monitoring. For guidance of intubation, as well as confirmation and monitoring, the pulsed laser light source can be transmitted through a stylet, a hollow endotracheal exchange catheter, a rigid laryngoscope, a fiberoptic endoscope or incorporated into or transmitted through the endotracheal tube itself. Optoacoustic technology can either be developed as a stand-alone device or can be incorporated into and improve existing technology.

Figure 4A:
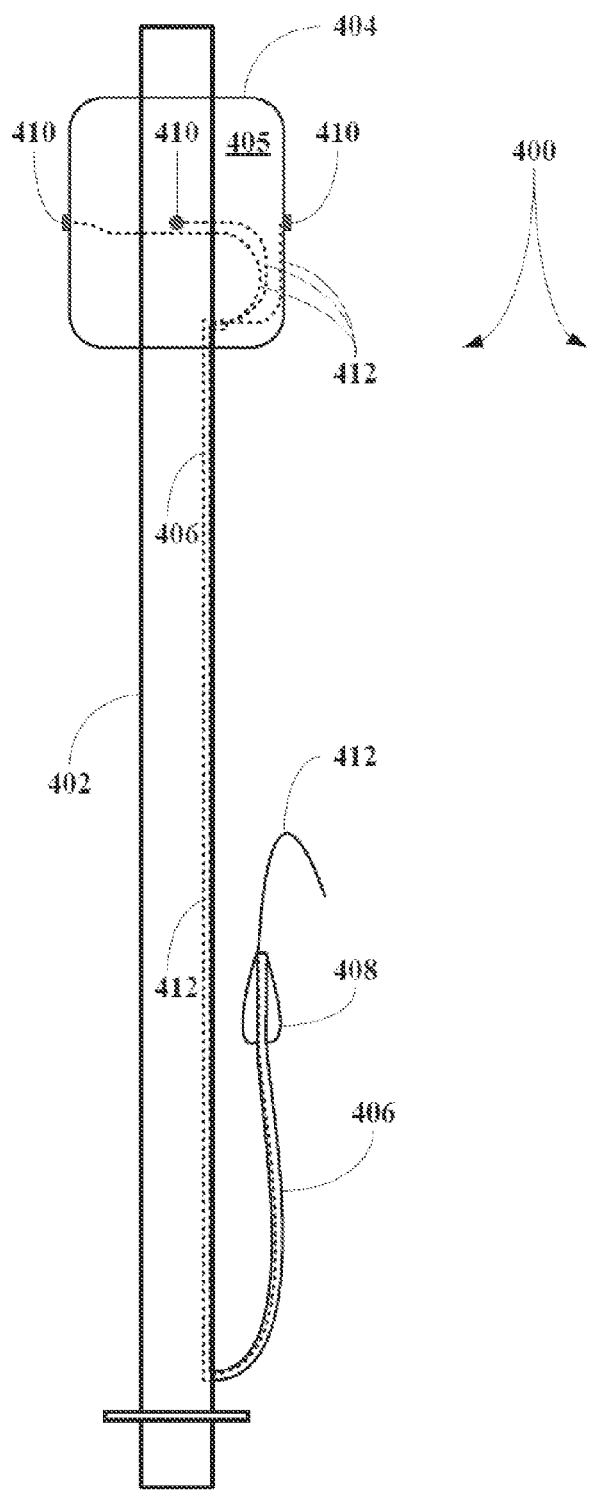
FIGS. 4A-B depict two embodiments of an endotracheal apparatus of this invention.

Referring now to FIGS. 4A and B, two embodiments of endotracheal units of this invention, generally 400, are shown. Looking at FIG. 4A, unit 400 includes endotracheal tube 402 having cuff 404 and inflation tube 406 having an end fitting 408. Tube 402 and cuff 404 are designed to be disposed in a trachea of a human or other animal. Cuff 404 includes a plurality of optical components 410 (four in all, three visible, one hidden and not shown) disposed on an outer surface 405 of cuff 404. Optical components 410 are in light communication with a light source (not shown) via optical conduits 412. In this, embodiment, light conduit 412 is inserted into inflation tube 406.

Figure 4B:
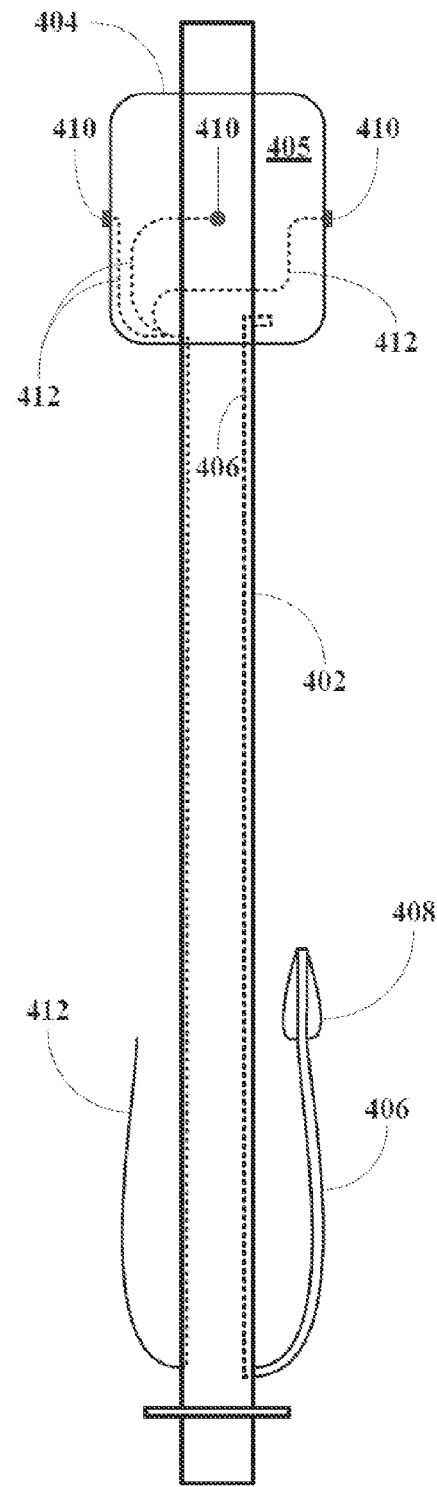

Looking at FIG. 4B, unit 400 includes an endotracheal tube 402 having cuff 404 and inflation tube 406 having an end fitting 408. Tube 402 and cuff 404 are designed to be disposed in a trachea of a human or other animal. Cuff 404 includes a plurality of optical components 410 (four in all, three visible, one hidden and not shown) disposed on an outer surface 405 of cuff 404. Optical components 410 are in light communication with a light source (not shown) via optical conduits 412. In this, embodiment, light conduit 412 is disposed inside the tube 402, but is not inserted inside the inflation tube 406.

In certain embodiments indwelling device including light conduit is a disposable single use unit that is adapted to be connected to a separate light source that is reusable between patients. In other embodiments, the light source is a diode and the light is generated inside the tissue without need for a light conduit from outside the patient's body.

Optoacoustic guidance of endotracheal intubation and confirmation and monitoring of endotracheal tube position according to the disclosed embodiments will achieve the aforementioned desirable attributes.

Example 1

An embodiment of an endotracheal tube apparatus as disclosed herein including a pulsed laser light source, a light conduit, a light exit port and an acoustic detector was tested to demonstrate that a signal obtained by positioning a pulsed laser light exit port within an endotracheal tube in a sheep with an acoustic detector positioned on an anterior neck to permit non-invasive accurate confirmation and maintenance of the tube location in the sheep.

Laser optoacoustic imaging combines the merits of optical tomography (high optical contrast) and ultrasound imaging (minimal scattering of acoustic waves) to yield high contrast, sensitivity, and resolution. Certain of the present inventors have developed laser optoacoustics as a technique for tissue characterization and diagnostic imaging. See e.g. Esenaliev R O, et al. "Laser opto-acoustic tomography for medical diagnostics: Experiments with biological issues" *SPIE Proc.* 1996; 2676: 84-90. Optoacoustic techniques utilize sensitive detection of laser-induced ultrasonic waves, which travel with minimal scattering through tissue in a straight line from the source to the transducer.

Absorption of light energy in a medium is followed by rapid thermal relaxation and a slight temperature increase in the medium. Thermal expansion of the irradiated medium induces mechanical stress (pressure rise). This mechanism is referred to as the thermo-optical mechanism of pressure generation. A short optical pulse with the incident fluence, $F_o$, induces a pressure rise, $P(z)$, in the medium upon condition of stress confinement.

One mathematical depiction of this relationship is shown in Eq. 1:

$$P(z) = (\beta c_s^2/C_p)\mu_a F = \Gamma\mu_a F(z) = \Gamma\mu_a F_o \exp(-\mu_a z) \quad \text{(Eq. 1)}$$

where $\beta$ [1/° C.] is the thermal expansion coefficient; $c_s$ [cm/s] is the speed of sound; $C_p$ [J/g° C.] is the heat capacity at constant pressure; $F(z)$ [J/cm$^2$] is the fluence of the optical pulse; and $\mu_a$ [cm$^{-1}$] is the absorption coefficient of the medium.

The optoacoustic pressure in Eq. 1 can be expressed in J/cm$^3$ or in bar (1 J/cm$^3$=10 bar). The expression $(\beta c_s^2/C_p)$ in Eq. 1 represents the dimensionless Grüneisen parameter, $\Gamma$. The exponential attenuation of the optical radiation in the medium is represented by $\exp(-\mu_a z)$. The condition of stress confinement means that there is insignificant stress relaxation in the irradiated volume during the optical pulse. To provide this condition, the duration of the optical pulse should be shorter than the time of stress propagation out of the irradiated volume.

Nanosecond laser pulses can be used to generate conditions of stress confinement for most optoacoustic applications including monitoring of [Hb] and hemoglobin saturation and exogenous dyes. The various species of Hgb (oxyhemoglobin, deoxyhemoglobin, carboxyhemoglobin and methemoglobin) have high absorption coefficients in the visible and NIR spectral range as do many dyes, such as indocyanine green, indigo carmine and methylene blue, that are approved for human use and clinically used inks such as those used for skin marking before plastic surgery. The high z-axial (depth) resolution of the optoacoustic technique permits direct measurement of the depth of the pigmented marker or, in the present approach, the depth of the tissue boundary at which the acoustic signal is generated by the absorption of the optical signal by tissue water.

Figure 5:
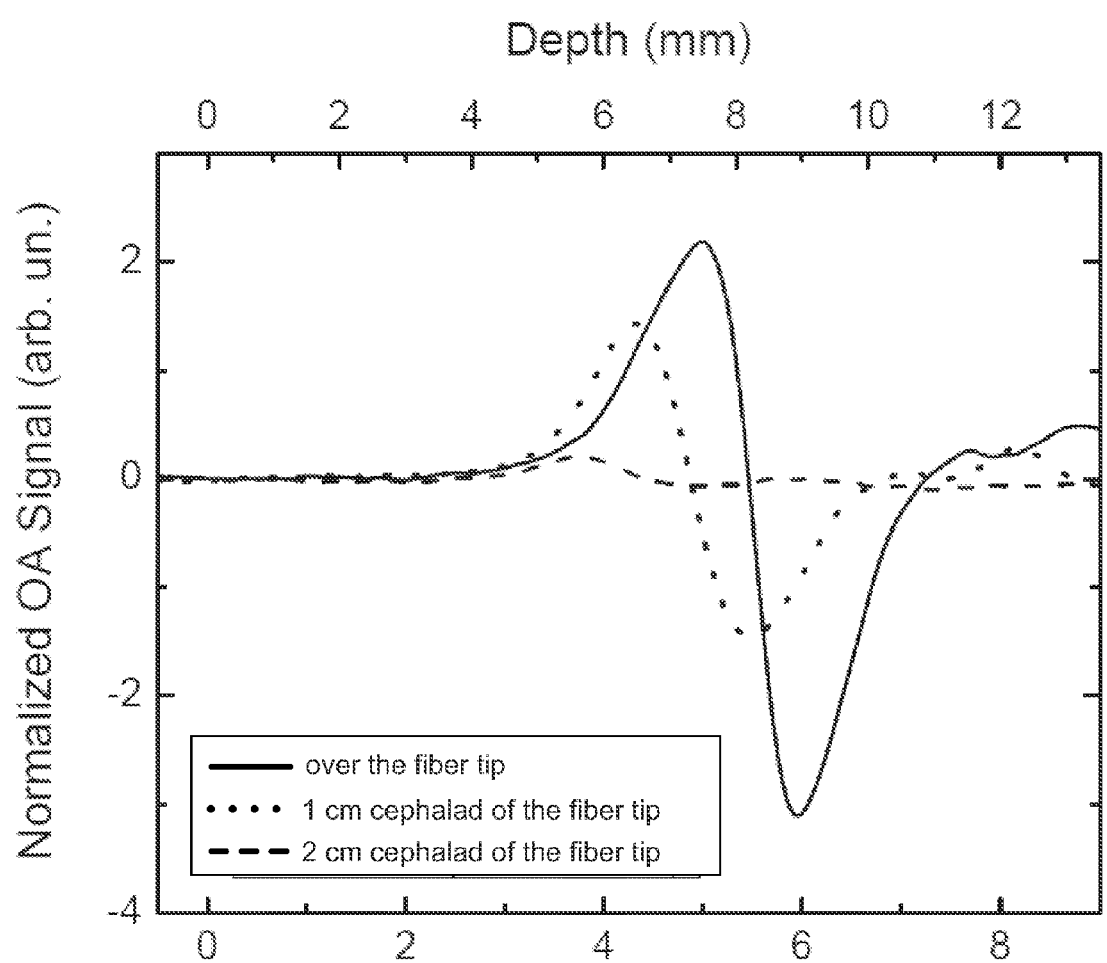
FIG. 5 depicts optoacoustic signals recorded from an optoacoustic detector using a 1.0 mm optical fiber placed within an endotracheal tube to the depth of the middle of a cuff.
Figure 7:
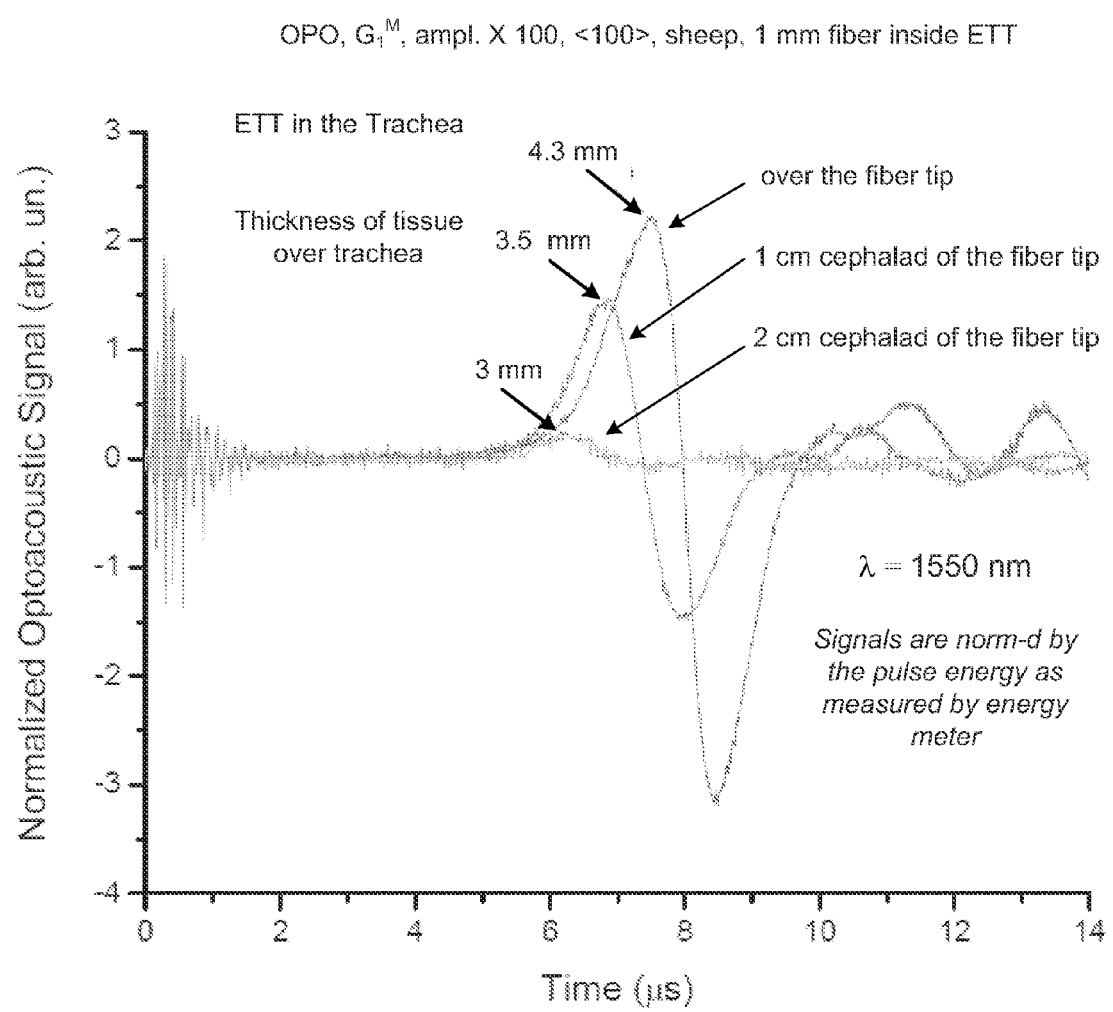
FIG. 7 depicts raw data of an optoacoustic spectrum of a 1.0 mm optical fiber placed within an endotracheal tube to the depth of the middle of a cuff.

Referring now to FIG. 5, a typical pattern obtained by optoacoustic monitoring showing diminishing signals when the detector is moved away from the endotracheal tube. The essentially same pattern would be obtained if the detector was stationary in the desired location and the endotracheal tube was deviated from proper placement. FIG. 7 shows a raw data trace of a 1.0 mm optical fiber placed within the endotracheal tube to the depth of the middle of the cuff. A pulse laser light source generating light at a wavelength of 1550 nm was connected to the optical fiber. The light source was a compact optical parametric oscillator (OPO) (Opolette 532 II, Opotek Inc., Carlsbad, Calif.). The OPO provided pulsed tunable Near-Infrared (NIR) radiation in the range of 680-2400 nm with pulse duration of 10 nanoseconds (ns) and repetition rate of 20 Hz. A sensitive, wide-band acoustic detector/transducer G1$^M$ was designed and built, including a piezoelectric element (8 mm in diameter with a central frequency of 0.8 MHz) for optoacoustic wave detection. The optoacoustic signals were amplified with a low-noise 17-dB preamplifier (model AH-17 DB, Onda Corp., Sunnyvale, Calif.) and a low-noise 40-dB amplifier (model 322-9-50, Analog Modules Inc., Longwood, Fla.) and then digitized with a 50-MHz 8-bit digitizer (NI USB-5132, National Instruments Corp., Austin, Tex.). The 40-dB amplification resulted in 100-fold (100×) amplification of the signal. One hundred signals were averaged to increase signal-to-noise ratio. Each optoacoustic signal shown in FIG. 7 was an average of the 100 signals each of them generated by one laser pulse (<100). The acoustic detector was then moved one cm cephalad and two cm cephalad with the peak signal obtained when the optoacoustic (OA) detector was located directly over the fiber tip and with progressively diminishing signals as the detector was moved further away toward the head. These data demonstrate the ability of OA technology to detect small cephalad or caudad movement of an endotracheal tube. FIG. 7 further shows, via the raw data trace, the strong signal detected when the optical emitter and acoustic detector are properly aligned over the trachea.

Figure 6:
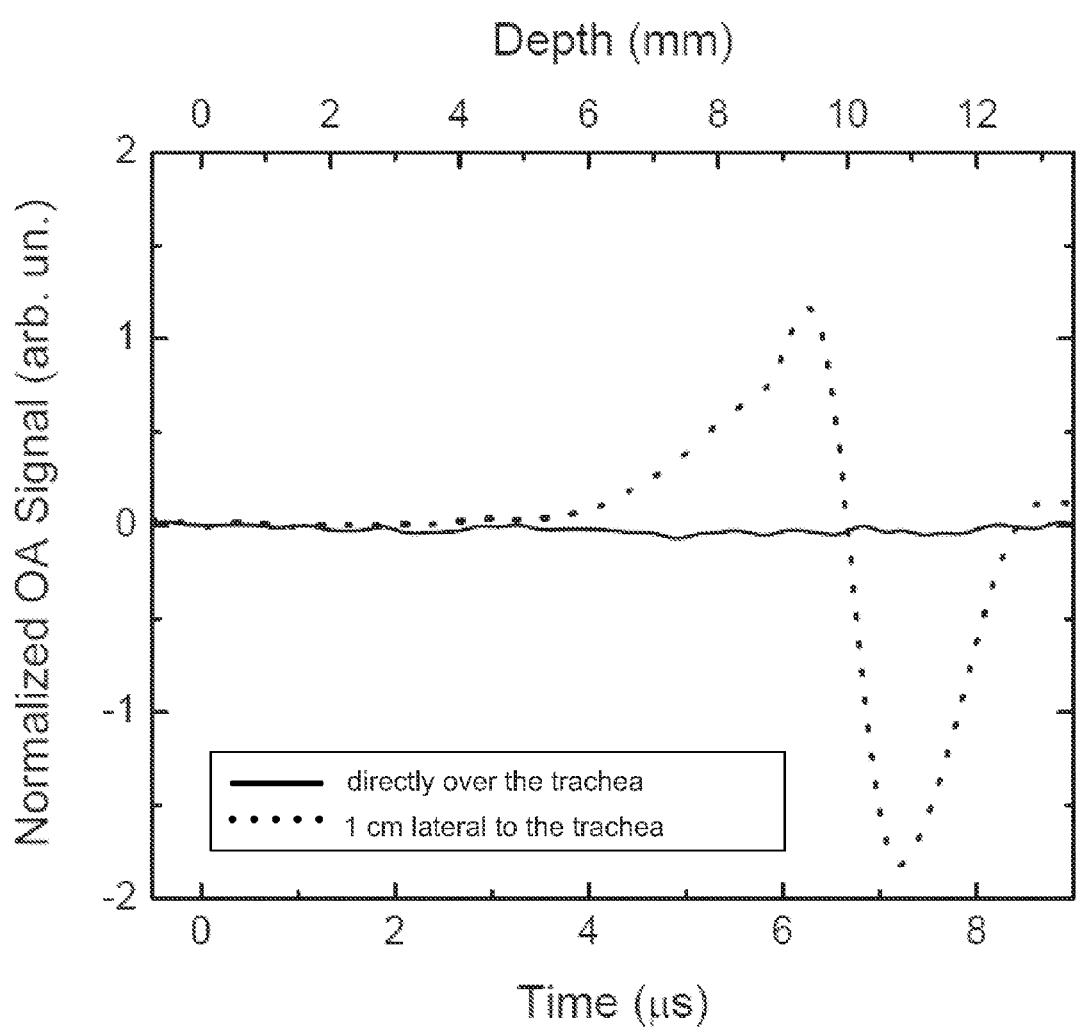
FIG. 6 depicts optoacoustic signals recorded from the optoacoustic (OA) detector when the optical fiber was inserted into the esophagus (solid line) to simulate a misplaced endotracheal tube.

Referring now to FIG. 6, a typical pattern recorded from the optoacoustic (OA) detector is shown when the optical fiber is misplaced by insertion into the esophagus (solid line; to simulate a misplaced endotracheal tube). When the OA detector is moved laterally, a signal is detected from the esophagus (hatched line). The lack of a signal over the trachea combined with the presence of a signal laterally is diagnostic of misplacement in the esophagus.

Figure 8:
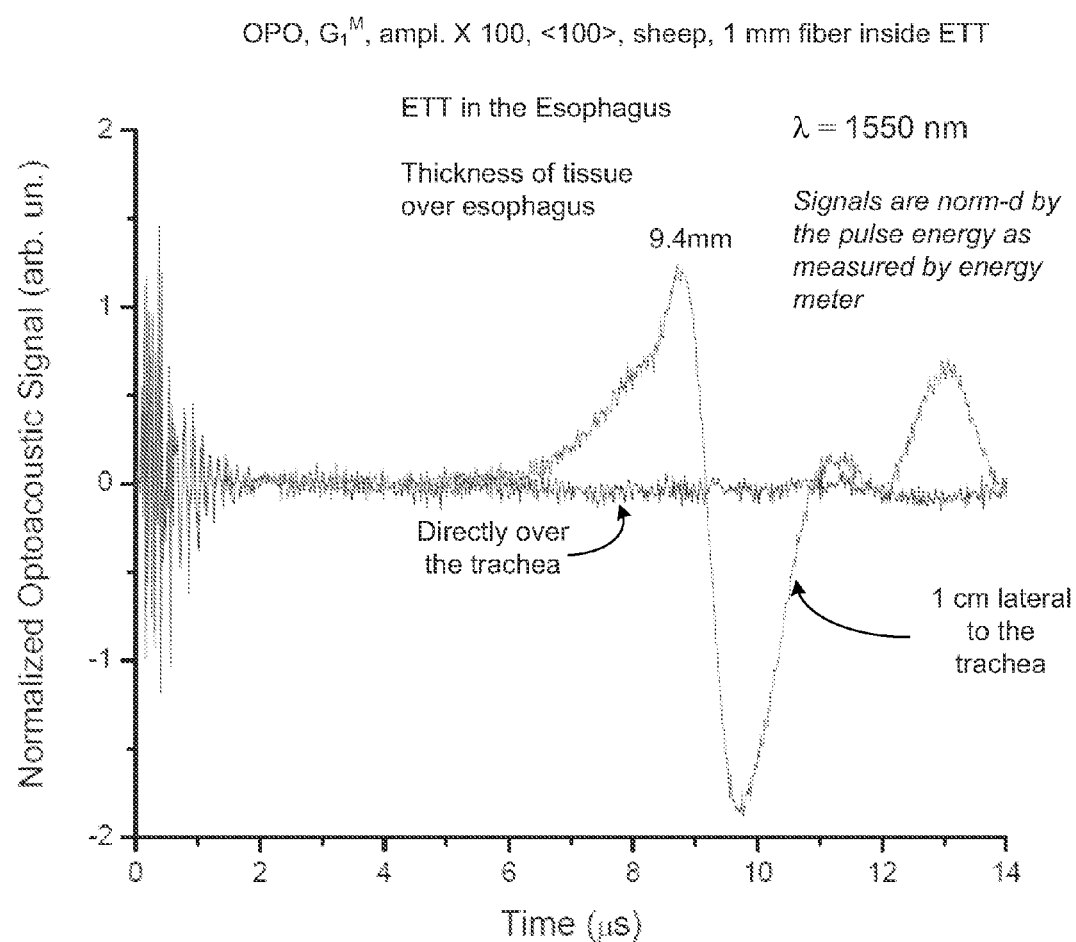
FIG. 8 depicts raw data of an optoacoustic spectrum of a typical pattern recorded from the optoacoustic (OA) detector when the optical fiber was inserted into the esophagus (solid line; to simulate a misplaced endotracheal tube).

In FIG. 8, which used the same conditions and equipment as described in reference to FIG. 7, the ETT including transmitter is placed in the esophagus and shows the trace obtained in this misplacement event. As indicated, there is no signal where the detector is placed over the trachea but a strong signal at 1 cm lateral to the trachea. This replicates the type of diagnostic readout that would be obtained in event of misplacement in the esophagus. As is apparent from these examples, the data obtained and displayed using the optoacoustic method provides clinically effective measurements of proper endotracheal tube placement and position monitoring.

The optoacoustic apparatus and techniques disclosed herein are ideally suited for monitoring foreign bodies in tissues and in hollow organs such GI organs and blood vessels. The apparatus and techniques may be used in combination with other modalities (including, but not limited to, radiofrequency, microwave, ultrasound, and pure optical methods, or their combination) for guidance and confirmation of placement of foreign bodies including endotracheal tubes in human and other animal bodies or tissues. Endotracheal tube placement is a specific example of placement of a medical device or foreign body within tissues with the subsequent need to non-invasively confirm correct placement. Optoacoustic technology is further ideally suited to any clinical situation in which a foreign body is placed for medical purposes, e.g., intravascular catheters, urinary bladder catheters, drainage tubes or prosthetic devices, and in which subsequent noninvasive confirmation of proper placement is required.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

The invention claimed is:

1. A system for real-time placement tracking of an endotracheal tube, comprising:
   an endotracheal tube comprising a cuff having an outer surface;
   an optical component mounted to the outer surface of the cuff of the endotracheal tube cuff and adapted to emit light into tissue surrounding the trachea into which the endotracheal tube is inserted to induce ultrasonic pressure waves within the tissue;
   an external acoustic detector adapted to receive the ultrasonic pressure waves induced in the tissue;
   an analyzer in electrical communication with the external acoustic detector, wherein the analyzer is configured to produce an output based on the received ultrasonic pressure waves that indicates whether or not the endotracheal tube cuff is positioned within the mid-trachea; and a display screen in electrical communication with the analyzer, wherein the display screen is configured to display the output from the analyzer as a graphical waveform that indicates whether or not the endotracheal tube is positioned within the mid-trachea.

2. The system of claim 1, further comprising a light conduit in optical communication with the optical component and adapted for connection to, and transmittal of light from, a light source external to the patient's body.

3. The system of claim 2, wherein the light conduit is a fiber optic.

4. The system of claim 1, wherein the optical component includes a light source that is adapted to generate light locally from inside the patient's body.

5. The system of claim 1, wherein the light is pulsed laser light.

6. The system of claim 1, wherein the light has a wavelength from about 750 nm to about 2500 nm.

7. The system of claim 1, wherein the analyzer generates a range of audible signals including a safety tone that indicates desired placement of the endotracheal tube and an alarm tone that indicates improper placement of the endotracheal tube.

8. The system of claim 1, wherein the external acoustic detector comprises a plurality of external acoustic detectors.

9. The system of claim 1, wherein multiple optical components are mounted to the outer surface of the cuff of the endotracheal tube at different positions around the periphery of the cuff.

10. The system of claim 1, wherein the optical component comprises a light-emitting diode.

11. The system of claim 1, wherein the graphical waveform results from plotting the output as a normalized optoacoustic signal as a function of depth.

12. A method of real-time placement tracking of an endotracheal tube comprising:

inserting into the trachea an endotracheal tube that includes an optical component mounted to an outer surface of a cuff of the endotracheal tube;

applying an external acoustic detector to an external surface of a patient on a region overlying the tissue;

applying power to the optical component to cause it to emit light into the tissue to induce ultrasonic pressure waves within the tissue;

receiving the induced ultrasonic pressure waves with the external acoustic detector;

producing an output with the analyzer that is based on the received ultrasonic pressure waves and that indicates whether or not the endotracheal tube cuff is positioned within the mid-trachea; and displaying the output from the analyzer as a graphical waveform on a display screen that is in electrical communication with the analyzer, wherein graphical waveform indicates whether or not the endotracheal tube is positioned within the mid-trachea.

13. The method of claim 12, further comprising monitoring the output of the analyzer on a periodic basis for as long as the endotracheal tube is in place.

14. The method of claim 12, further comprising monitoring the output of the analyzer on a continuous basis for as long as the endotracheal tube is in place.

15. The method of claim 12, wherein the light has a wavelength from about 750 nm to about 2500 nm.

16. The method of claim 12, wherein the analyzer generates a range of audible signals including a safety tone that indicates desired placement of the endotracheal tube and an alarm tone that indicates improper placement of the endotracheal tube.

17. The method of claim 12, further comprising an initial step of affixing the optical component to the endotracheal tube.

18. The method of claim 12, wherein the graphical waveform results from plotting the output as a normalized optoacoustic signal as a function of depth.

* * * * *